US011248015B2

(12) United States Patent
Park et al.

(10) Patent No.: US 11,248,015 B2
(45) Date of Patent: Feb. 15, 2022

(54) METHOD FOR PREPARING PSICOSE USING RECYCLING

(71) Applicant: SAMYANG CORPORATION, Seoul (KR)

(72) Inventors: Ji Won Park, Suwon-si (KR); Sung Won Park, Yongin-si (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 541 days.

(21) Appl. No.: 16/463,986

(22) PCT Filed: Nov. 22, 2017

(86) PCT No.: PCT/KR2017/013368
§ 371 (c)(1),
(2) Date: May 24, 2019

(87) PCT Pub. No.: WO2018/105931
PCT Pub. Date: Jun. 14, 2018

(65) Prior Publication Data
US 2020/0385415 A1 Dec. 10, 2020

(30) Foreign Application Priority Data
Dec. 8, 2016 (KR) .................. 10-2016-0167050

(51) Int. Cl.
| C07H 1/06 | (2006.01) |
| C07H 3/00 | (2006.01) |
| C12P 19/00 | (2006.01) |
| B01D 9/00 | (2006.01) |
| B01D 15/18 | (2006.01) |
| B01D 15/36 | (2006.01) |
| C07H 3/02 | (2006.01) |
| C12P 19/02 | (2006.01) |
| C12P 19/24 | (2006.01) |

(52) U.S. Cl.
CPC .............. *C07H 1/06* (2013.01); *B01D 9/0059* (2013.01); *B01D 15/185* (2013.01); *B01D 15/361* (2013.01); *C07H 3/02* (2013.01); *C12P 19/02* (2013.01); *C12P 19/24* (2013.01); *B01D 2009/0086* (2013.01)

(58) Field of Classification Search
CPC .............. C07H 1/06; C07H 3/02; C12P 19/02
See application file for complete search history.

(56) References Cited

U.S. PATENT DOCUMENTS

| 2,985,589 A | 5/1961 | Broughton et al. |
| 2011/0237790 A1* | 9/2011 | Lee .......................... C07H 1/06 536/127 |

FOREIGN PATENT DOCUMENTS

| CN | 106520863 | 3/2017 | |
| EP | 1834957 | 9/2007 | |
| JP | 2001-354690 | 12/2001 | |
| JP | 2011-206054 | 10/2011 | |
| JP | 2016-523526 | 8/2016 | |
| JP | 2017-532382 | 11/2017 | |
| JP | 2019-500050 | 1/2019 | |
| KR | 10-2011-0108185 | 10/2011 | |
| KR | 10-2011-0126719 | 11/2011 | |
| KR | 10-1318422 | 10/2013 | |
| KR | 10-2014-0021974 | 2/2014 | |
| KR | 10-2014-0054997 | 5/2014 | |
| KR | 10-2014-0080282 | 6/2014 | |
| KR | 10-2014-0123284 | 10/2014 | |
| KR | 10-2016-0024193 | 3/2016 | |
| KR | 10-2016-0046143 | 4/2016 | |
| KR | 10-2016-0062349 | 6/2016 | |
| KR | 20160062349 A * | 6/2016 | ............... C07H 3/02 |
| KR | 10-1723007 | 4/2017 | |
| TW | 201619177 | 6/2016 | |
| WO | 2017-150766 | 9/2017 | |

OTHER PUBLICATIONS

EPO, Extended European search report of EP 17878321.3 dated Jun. 30, 2020.
Park, Jong-Uk et al., "Construction of Heat-Inducible Expression Vector of Corynebacterium glutamicum and C. ammoniagenes: Fusion of λ Operator with Promoters Isolated from C. ammoniagenes", J. Microbiol. Biotechnol., 18 (4):639-647, 2008.
Nina Wagner, "Integration of biocatalysis and simulated moving bed chromatography for the high-yield production of rare sugars", Doctor of Science of ETH Zurich, Switzerland, 2014.

* cited by examiner

*Primary Examiner* — Sikarl A Witherspoon
(74) *Attorney, Agent, or Firm* — Lex IP Meister, PLLC

(57) ABSTRACT

The present invention relates to a method for preparing psicose by effectively utilizing a psicose crystallization mother liquor obtained in a psicose crystallization process, and specifically, relates to a method of preparation of psicose by putting a psicose crystallization mother liquor obtained in a psicose crystallization process into one or more kinds of processes selected from the group consisting of activated carbon treatment, ion purification process, simulated moving bed chromatography separation process and concentration process of psicose fraction to recycle.

14 Claims, 1 Drawing Sheet

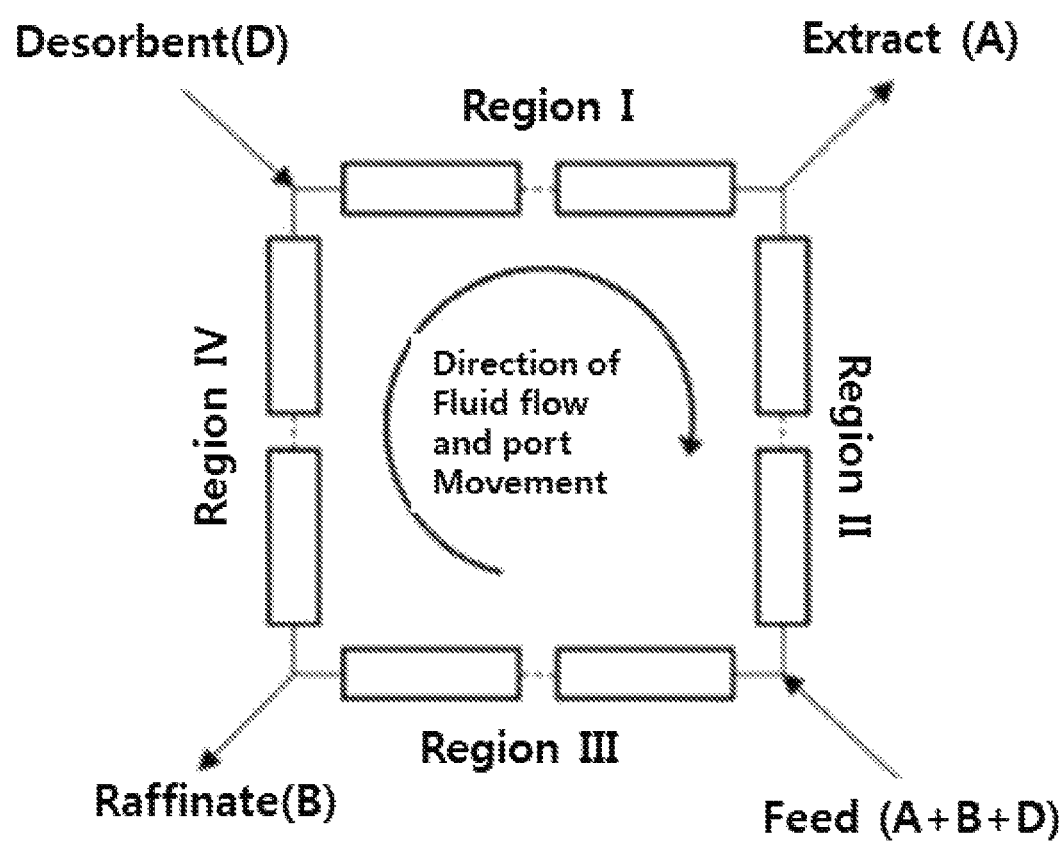

METHOD FOR PREPARING PSICOSE USING RECYCLING

TECHNICAL FIELD

The present invention relates to a method for preparing psicose by recycling a psicose crystallization mother liquor obtained in a psicose crystallization process, and specifically, relates to a method of preparation of psicose by putting a psicose crystallization mother liquor obtained in a step of psicose crystallization in a psicose preparation process into a separation process of psicose conversion product to utilize and an apparatus of preparation of psicose used for the same.

BACKGROUND ART

Psicose is an epimer of fructose (D-fructose) and is one kind of functional saccharides known as a rare saccharide, and it has been known to have an effect on prevention and improvement of diabetes, since it has sweetness of about 60 to 70% of sugar and almost zero calorie. In addition, psicose is known to have excellent solubility, and it is one of materials where utilization for food is attracting attention.

There are a chemical method and a biological method in the method for preparing psicose, and recently, a method for preparing psicose with a biological method performs psicose conversion reaction by contacting fructose-containing substrate solution with a psicose epimerase or a microorganism producing the enzyme. However, it is required to separate psicose with high purity, since the reaction solution comprising D-psicose is low purity product.

The reaction raw material used for the psicose conversion process may be fructose isomerization reactant obtained by isomerization reaction of glucose obtained from degradation of starch, etc.

Since the conversion rate of enzymatic reaction of psicose produced from fructose is 20 to 30% (w/w), it shows process flow in which the amount of mother liquor generated is more than the amount of products of psicose. Consequently, the generation of large amount of mother liquor shows a non-economical problem in the industrial production by increasing the production cost due to decline of psicose production.

Thus, a method for enhancing the production yield of psicose by recycling the psicose crystallization mother liquor is required, since the psicose crystallization mother liquor is obtained in the psicose crystallization process and this comprises a high concentration of psicose.

DISCLOSURE

Technical Problem

One example of the present invention relates to a method for preparing psicose by recycling the psicose crystallization mother liquor obtained in the psicose preparation process into the psicose separation process and an apparatus used for the same, in order to enhance the yield of psicose that is a target product and increase the availability of raw material by utilizing the psicose crystallization mother liquor obtained in the psicose preparation process.

Technical Solution

The present invention relates to a method for preparing psicose by recycling the psicose crystallization mother liquor obtained in the preparation process of psicose crystals into the psicose separation process and an apparatus used for the same.

It is a method for enhancing the purity and yield of psicose and increasing the availability of raw material by recycling the psicose crystallization mother liquor, since the psicose is comprised at a high concentration in the psicose crystallization mother liquor obtained in the crystallization process of psicose.

One embodiment of the present invention relates to a method for preparing psicose in which the psicose crystallization mother liquor obtained in the preparation of psicose crystals is put into the psicose separation process and used for the psicose preparation.

The psicose crystallization mother liquor may be obtained by obtaining the psicose fraction in the SMB chromatography separation process and obtaining psicose concentrates by ion purifying and concentrating the psicose fraction, and preparing psicose crystals from the concentrates.

The psicose separation process may comprise one or more kinds of processes selected from the group consisting of activated carbon treatment, ion purification and simulated moving bed (SMB) chromatography separation process, and it may recycle the psicose crystallization mother liquor by putting it into the separation process.

The psicose crystallization mother liquor according to the present invention has an advantage of increasing the production of high purity psicose as increasing the separation yield in the simulated moving bed chromatography separation process by putting it into the separation process, since it has higher psicose content than the psicose conversion reactant, and the availability of raw material can be increased by recycling the psicose crystallization mother liquor.

Hereinafter, the present invention will be described in more detail.

One embodiment of the present invention relates to a method of preparation of psicose, wherein the psicose crystallization mother liquor is put into the psicose separation process and used for preparing psicose.

The psicose crystallization mother liquor means a solution remained after preparing psicose crystals by using the psicose solution, and may further comprise washing water obtained after washing the psicose crystals. For example, it may prepared with a solution remained after preparing psicose crystals by crystallizing the psicose solution and removing crystals with a solid-liquid separation method such as centrifugation, etc. In specific one embodiment, the psicose crystallization mother liquor may be obtained by obtaining the psicose fraction in the simulated moving bed (SMB) chromatography separation process in the preparation method of psicose and obtaining the psicose concentrates by ion purifying and concentrating the psicose fraction and preparing psicose crystals from the concentrates.

One embodiment of preparation of psicose crystals may comprise the primary ion purification, high purity chromatography separation, the secondary ion purification, concentration and crystallization processes, and selectively, may perform an activated carbon treatment process, an ion purification process, or both activated carbon treatment process and ion purification process of psicose conversion product.

In the preparation method of psicose, to obtain a high purity psicose product from psicose conversion reaction solution, a high purity separation process may be performed, and in addition, to obtain psicose crystals, a psicose crystallization process may be performed by using a high purity of psicose syrup. Since the conversion rate of enzymatic reaction of psicose produced from fructose is 15 to 30% (w/w), it shows process flow in which the amount of mother liquor generated is more than the amount of products of psicose. Thus, as the psicose crystallization mother liquor obtained in the psicose crystallization process comprises a high concentration of psicose, the production yield of psicose can be enhanced by recycling it.

The psicose crystallization mother liquor may comprise 80% by weight or more psicose based on 100% by weight of total content of solid, and for example, may comprise 80 to 99% by weight, preferably 85 to 96% by weight.

The method for preparing psicose according to the present invention comprises a process for putting the psicose crystallization mother liquor obtained in the psicose crystallization process into the psicose separation process where the primary ion purification and separation using a simulated moving bed (SMB) chromatography are performed to the conversion reactant to obtain the psicose fraction and fructose raffinate. The psicose separation process may consist of a separate single process or may be comprised as one process constituting the psicose preparation process.

For example, when the psicose separation process wherein the psicose crystallization mother liquor is put is comprised in the psicose preparation process, the method for preparing psicose of the present invention may comprise (1) a psicose conversion process which prepares psicose conversion product; (2) a psicose separation process which performs the primary ion purification and separation using a simulated moving bed (SMB) chromatography to psicose conversion product, thereby obtaining psicose fraction and fructose raffinate; (3) a process for obtaining concentrates by ion purification and concentration of the psicose fraction; (4) a process for obtaining psicose crystals and psicose crystallization mother liquor by using the psicose concentrates; and (5) a process for recycling the psicose crystallization mother liquor by putting it into the psicose separation process of the step (2).

The process of preparation of psicose of the present invention may use both continuous and batch processes, preferably a continuous process.

It may further comprise a step of obtaining fructose raffinate in the SMB chromatography separation process and treating the fructose raffinate with one or more kinds of processes selected from the group consisting of cooling, pH adjustment, ion purification and concentration processes, thereby recycling it as a raw material of psicose conversion reaction.

In one embodiment of the present invention, the method for preparing psicose according to the present invention, when the psicose separation process consists of a separate single process in which the psicose crystallization mother liquor obtained in the psicose crystallization process is put into the psicose separation process wherein the primary ion purification and separation using the simulated moving bed (SMB) chromatography are performed to psicose conversion product, thereby obtaining psicose fraction and fructose raffinate, may comprise only the following (2) separation process of psicose conversion reactants, and may prepare psicose by further comprising (2) purification and concentration processes of psicose. Otherwise, the psicose separation process may comprise both the following (2) and (3), thereby preparing psicose crystals.

When the psicose separation process is comprised as one process constituting the psicose preparation process, psicose may be prepared via the following (1) to (3) processes. Otherwise, psicose crystals may be prepared via the following (1) to (4) processes.

Hereinafter, the process of psicose preparation including the recycling of fructose raffinate obtained in the high purity separation process for the psicose conversion product according to the present invention will be described in detail by each step.

(1) Psicose Conversion Process

The psicose conversion process is a process for obtaining psicose from the fructose-containing raw material by performing a psicose conversion reaction, and produces a reaction solution including psicose as reaction product converted from fructose.

In one specific embodiment of the present invention, the method for preparing psicose according to a biological method may culture a strain producing psicose epimerase or a recombinant strain including a gene encoding the psicose epimerase and reacts the psicose epimerase obtained from that with a fructose-containing raw material to produce psicose. The psicose epimerase reaction may be performed in a liquid phase reaction or a solid phase using an immobilization enzyme.

Otherwise, psicose may be produced by obtaining a strain producing psicose epimerase or a recombinant strain including a gene encoding the psicose epimerase, and reacting the fructose-containing raw material with a composition for psicose preparation comprising one or more selected from the group consisting of microbial cell of the strain, culture of the strain, lysate of the strain, and extract of the lysate or culture. When psicose is prepared by using the microbial cell of strain producing the psicose epimerase, it may be performed with a liquid phase reaction or a solid phase using an immobilized microbial cell.

In one specific embodiment of the present invention, the strain producing the psicose epimerase may be the strain which has high stability and can convert fructose to psicose at a high yield or produce the psicose epimerase. The strain may be a strain isolated from nature or its mutant strain, non-GMO strain, or a recombinant strain in which a gene encoding the psicose epimerase is introduced. In one embodiment of the present invention, various known strains as the non-GMO strain may be used. The recombinant strain may be prepared by using various host cells, for example, *E. coli, Bacillus* sp. strain, *Salmonella* sp. strain and *Corynebacterium* sp. strain, etc, but preferably, GRAS strain such as *Corynebacterium* sp. Strain, and may be *Corynebacterium glutaricum*.

The psicose conversion process according to the one embodiment of the present invention is performed by a biological method. For example, in case of solid phase reaction, it may further include a step of packing immobilizede psicose epimerase or microbial cell on a support into a column and a step of providing fructose solution into the packed column. The column being packed by the support-immobilized enzyme or microbial cell and the packing method may be performed according to easily selecting appropriate one by one skilled in the technical field where the present invention belongs according to the used enzyme or microbial cell, or immobilization carrier. In one specific embodiment of the present invention, a packed-bed column may be prepared by packing the immobilized enzyme or microbial cell into a column. An enzymatic reaction, that is, the conversion of fructose to psicose may be performed by providing a substrate of fructose solution to the packed-bed column.

In the conversion reaction of psicose, the reaction may be performed under the condition of pH 4.5 to 7.5, for example, pH 4.7 to 7.0, or pH 5.0 to 6.0 or pH 5.0 to 5.5. In addition, the reaction may be performed under the temperature condition of 30° C. or higher, for example 40° C. or higher. The enzyme activity for converting fructose to psicose (for example, epimerase) can be controlled by a metal ion, and therefore in the production of psicose, the conversion efficiency from fructose to psicose, in the production rate of psicose can be increased, when the metal ion is added. Thus, the composition for producing psicose may further comprise one or more of metal ions selected from the group consisting of copper ion, manganese ion, calcium ion, magnesium ion, zinc ion, nickel ion, cobalt ion, iron ion, aluminum ion, etc.

The detailed technical contents regarding psicose and its preparation method are disclosed in Korean patent publication No. 2014-0021974, Korean patent publication No. 2014-0054997, Korean patent publication No. 2014-0080282, or Korean patent No. 10-1318422.

The fructose as a raw material put into the psicose conversion process according to the present invention may be prepared by a biological method or chemical method, preferably by a biological method. The fructose as a raw material may be provided as a liquid phase raw material, or a powdery raw material such as fructose powder, and in case of fructose syrup, it may be the product obtained in the biological method or chemical preparation method, or one prepared by dissolving fructose powder in a solvent such as water.

In an embodiment of preparing the fructose raw material with a biological method, the fructose may be obtained by performing a fructose isomerization process which isomerizes a glucose-containing raw material with a fructose isomerase or a microbial cell producing the enzyme and separating it through the primary ion purification, high purity chromatography separation process, the secondary ion purification and concentration for the products of fructose isomerization process.

In the method for producing psicose, for effective production of psicose, the concentration of fructose used as a substrate may be 85 w/v % or higher, 90 w/v % or higher, or 95 w/v % or higher, for example, 85 to 99 w/v %, 88 to 99 w/v %, 88 to 99 w/v %, 85 to 87% (w/v), 88 to 90% (w/v), 91 to 93% (w/v), 94 to 99% (w/v) or 97 to 99% (w/v), based on the total reactants. The concentration of fructose may be decided by considering economics of process and solubility of fructose, and the fructose may be used as a solution prepared by dissolving fructose in a buffer solution or water (for example, distilled water).

To illustrate the fructose preparation process according to an example of the present invention, the fructose may be obtained from sugar or glucose. As a result, a method for preparing psicose at high yield by using generalized and inexpensive raw material such as glucose, fructose and sugar is provided, thereby enabling mass production of psicose.

To illustrate one embodiment of fructose preparation process of the present invention, the saccharification solution with 88% by weight or higher of glucose content is obtained by enzymatic hydrolysis, after mixing corn starch with water to be 30 to 35% by weight. Then, by passing a step of removing impurities of the saccharification solution and a fructose isomerization step, a fructose syrup with 40 to 44% by weight of fructose content is obtained. Then, glucose raffinate and fructose fraction are obtained by using a SMB chromatography and are passed through the secondary ion purification and concentration of the fructose fraction are performed, to produce n a fructose-containing solution with 85% by weight or higher, for example 85 to 99% by weight of fructose content. The SMB adsorption separation method is described in the following (2) item. The process for removing impurities may be performed by a step for removing insoluble materials, a step of decoloring by using activated carbon, and a step of passing solution into an ion exchange resin column for removing impurities of colored components and ion components, etc. The treatment of activated carbon may include the solution by treating with the activated carbon packed in column or the adding the activated carbon added to the reacting vessel A specific embodiment of fructose separation process may comprise the primary ion purification, a high purity chromatography separation, secondary ion purification, a concentration and a crystallization, and optionally carry out desalting, decoloring, or decoloring and desalting process of conversion product.

The concentration step included in the fructose preparation process of the present invention may be conducted with various methods, so as to be fructose content of 85% by weight or higher. For example, the fructose fraction obtained by the SMB adsorption separation method (for example, solid concentration of 20 to 30%) may be concentrated to be the solid concentration of 45 to 55% by weight through the concentration process.

(2) Separation Process of Psicose Conversion Product

The psicose preparation process according to the present invention may comprise a separation process of psicose conversion product, including ion purification and SMB chromatography separation process of the psicose conversion product. In one specific embodiment, the psicose conversion product is performed by SMB chromatography separation, thereby being separated to psicose fraction which has higher psicose content than psicose conversion product and fructose raffinate, and the psicose fraction is put into a concentration process or crystallization process.

It may comprise separation/purification so that the psicose content in the psicose fraction is 85% by weight or higher, 90% by weight or higher, 91% by weight or higher, 92% by weight or higher, 93% by weight or higher, 94% by weight or higher, or 95% by weight or higher, for example, 90 to 99% by weight, 95 to 98% by weight or 95% by weight to 99.3% (w/w). The fructose content of fructose raffinate obtained in the high purity separation process may be 85% by weight or higher, for example 85% by weight to 98% by weight, and it is preferable that the psicose content is 2% by weight or less. The content of saccharides including disaccharides or higher degree of polymerization other than fructose and glucose among fructose raffinate may be preferably less than 10% by weight based on the total solid content of the total saccharides. The saccharides including disaccharides or higher degree of polymerizations among impurities include maltose and isomaltose, etc., and may comprise maltose-related or isomaltose-related oligosaccharides.

The ion purification process in the psicose preparation process is a process for removing ion comprised in reactants, and it may be conducted before and/or after SMB chromatography separation process. The primary ion purification which performs ion purification process before conducting the SMB chromatography separation may be carried out by the same or different method with the following secondary ion purification of psicose fraction, and for example, it may be performed by using 1 or 2 or more separation columns packed with same kind or different kinds of ion exchange resin. The ion purification process may be performed at 35 to 50° C. temperature, for example, 38 to 58° C., considering physical properties of resin used for ion purification and ion purification efficiency.

The SMB chromatography separation process may be performed at the temperature of 45 to 70° C., for example, 50 to 65° C.

In one embodiment of the present invention, before performing the primary ion purification process of psicose conversion product, selectively, a process for treating the psicose conversion product with activated carbon may be further carried out. In addition, selectively, a process of concentration to be the solid content of 45 to 55% by performing a concentration process may be future carried out, before conducting the SMB chromatography separation process after performing the primary ion purification process. Thus, the separation process of psicose conversion product according to the present invention may comprise the primary ion purification process and SMB chromatography separation process of psicose conversion product, or activated carbon treatment, the primary ion purification process and SMB chromatography separation process of psicose conversion product, and selectively, may further perform a concentration process, before conducting the SMB chromatography separation process after the primary ion purification process.

In one embodiment of the present invention, the high purity separation step using SMB chromatography is a separation method useful for securing stability of materials, due to no phase change in the separation process. In these adsorption separation methods, a chromatography separation method has been used in abundance as a liquid phase adsorption separation method. Among them, a simulated moving bed (SMB) adsorption separation method is a separation technology proposed in U.S. Pat. No. 2,985,589 in 1961, and has an advantage that the purity and productivity are excellent and the use of less solvent is possible, compared to the conventional batch chromatography, by continuous separation using many of columns. The simulated moving bed (SMB) adsorption separation process is a process, in which injection of separation target mixture and production of raffinate and extract are implemented continuously.

The fundamental principle of SMB is to copy the flow of immobilized or moving counter-current and enable the continuous separation by moving positions between columns at regular intervals. The material which moves fast due to its weak affinity with an adsorbent moves in the direction of flow of liquid phase and collects in the extract, and the material which moves slowly due to its strong affinity with an adsorbent moves in the direction of flow of immobilized phase and collects in raffinate. Columns are connected continuously, and the inlet consists of mixture and moving phase, and the outlet consists of target extract and raffinate.

In the present specification, the term "raffinate" is also called as "residual solution". The products obtained from as a separation process which is provided by a feeding material include two fraction of a target fraction including a target material to increase its content by the separation process and a residual solution including a material to be removed or to reduce its content. In one embodiment of the present invention, the product obtained in the psicose conversion process is a mixture of fructose as a raw material and psicose as a product material. After the psicose conversion product is passed through the SMB chromatograph separation, the psicose fraction with increased content of psicose and the residual solution are produced. The fructose raffinate can be obtained, since fructose used as a reacting raw material is included at a large amount in the residual solution.

Since a cation exchange resin of strong acid in which a salt is added, which is widely used for a process of monosaccharide separation is used as a separation resin in the SMB, metal ions are comprised in products obtained after performing the separation process. An example of cation exchange resin of strong acid may be a cation exchange resin in which a calcium activated group is attached.

FIG. 1 shows a process chart of general simulated moving bed (SMB) adsorption separation apparatus. The general simulated moving bed (SMB) adsorption separation apparatus consists of adsorbent inlet port positioned in 4 sections consisting of one or more columns and between each section, an extract discharge port that is a strong absorbate, a separation target mixture (feed) inlet port and a raffinate discharge port that is a weak adsorbate. The separation method of mixture using similar simulated moving bed (SMB) adsorption separation apparatus may be applied for separation of mixture of aromatic hydrocarbons, separation process of ethyl benzene, separation process of chiral compounds, etc, and it may be applied for separation process of racemic mixture drugs which are final products or intermediates in the drug preparation process.

(3) Psicose Ion Purification and Concentration

The psicose fraction obtained in the high-purity separation process using SMB chromatography in the psicose preparation process of the present invention may be commercialized as liquid phase syrup through a psicose concentration process, or may be commercialized as psicose crystals through a psicose crystallization process. It is a step of preparing concentrates obtained by ion purifying and concentrating psicose fraction obtained in the SMB chromatography separation of the step (2). The concentrates may be used as a psicose syrup product or prepared for psicose crystals by putting into a crystallization process.

In one embodiment of the present invention, the secondary ion purification of psicose fraction obtained in the high purity separation process using SMB chromatography may be performed, and it may be performed by the same or different methods with the primary ion purification performed in the separation process.

The psicose content in the psicose solution for collecting psicose crystals should be contained at a high concentration in the supersaturation condition, but the psicose content of psicose conversion product is low, so direct crystallization for psicose conversion product cannot be conducted and a process of purification and concentration up to the desired level should be performed to increase the psicose content before the crystallization step.

In one specific embodiment of the present invention, the step of concentrating purified psicose solution may be performed at 55 to 75° C. When the temperature of concentrated solution is increased over 75° C., thermal modification of D-psicose may occur, and when decreased less than 55° C., desired level of concentration is difficult to achieve. Since the temperature of product is rapidly increased by evaporation heat as the concentration progresses, it should be concentrated rapidly by maintaining the temperature of concentrated solution to 75° C. or lower.

In one specific embodiment of the present invention, in order to achieve thermal modification of psicose and desired level of concentration, it may be concentrated in the range of 55 to 75° C. temperature, preferably 60 to 70° C. The concentration process may be conducted once or twice or more repeatedly until achieving the desired concentration level.

Specifically, the concentration process of psicose fraction obtained in the SMB chromatography separation process may be performed by various methods, and the solid content in the concentrates may be 70 Brix or higher. For example, the psicose fraction obtained by the SMB adsorption separation method (for example, solid content 20 to 30% by weight) may be concentrated to the solid content of 70 Brix or higher through the concentration process. The solid content in the psicose concentrates may be 70 Brix or higher, for example, 70 Brix to 85 Brix.

The concentration process in the psicose preparation process may comprise concentrating in the temperature range of 55 to 75° C. for 10 to 15 min. The concentration may concentrate under decompressed or vacuumed conditions by using a falling film evaporator or thin film evaporator.

The psicose content comprised in the psicose concentrates is almost same as psicose content of psicose fraction obtained in the SMB chromatography separation process, and the solid content is increased, thereby enabling the crystallization process to perform. The psicose content comprised in the psicose concentrates may be 94% by weight or higher, 95% by weight or higher, 96% by weight or higher, 97% by weight or higher, 98% by weight or higher, or 99% by weight or higher, based 100% by weight of the solid total content.

(4) Crystallization of Psicose Concentrates

In one specific embodiment of the present invention, the method for preparing psicose crystals may comprise a step of the secondary ion purification of psicose fraction obtained in the SMB chromatography separation process, a step of concentrating the ion purified psicose fraction, and a step of crystallizing psicose from the concentrates to obtain psicose crystals and psicose crystallization mother liquor, and selectively, may further comprise a recovering process, a washing process and a drying process of psicose crystals.

The specific embodiment of preparation of psicose crystals may comprise the primary ion purification, SMB chromatography separation, the secondary ion purification, concentration and crystallization processes, and selectively, may perform an activated treatment process, an ion purification process, or both activated treatment process and ion purification process to the psicose conversion product.

The method for preparing psicose crystals according to the present invention may implement crystallization by regulating temperature and concentration of psicose concentrate solution, and specifically the supersaturated state may be maintained by declining the temperature of psicose solution or changing the concentration of D-psicose in D-psicose solution. In one specific embodiment of the present invention, the crystallization progress may be monitored by observing samples taken at regular intervals in the crystallization step with naked eyes or a microscope or analyzing the sugar concentration in supernatant collected from centrifugation of samples, and according to the result, the temperature or concentration of D-psicose may be controlled. When the psicose concentrated solution is cooled and crystallized to prepare psicose crystals, the crystal growth may be induced by repeatedly conducting temperature rising and cooling, after rapidly cooling in the temperature range of 10 to 25° C. through a heat exchanger.

The method for preparing psicose crystals according to the present invention may further comprise various solid-liquid separations, for example, a step of recovering by centrifugation, a step of washing with deionized water, and a step of drying. The drying step may be performed in a fluidized bed drier or vacuum drier, but not limited thereto. The psicose comprised in the psicose crystals may be 94% by weight or higher, 95% by weight or higher, 96% by weight or higher, 97% by weight or higher, 98% by weight or higher, or 99% by weight or higher, based on 100% by weight of the total solid content.

The psicose crystallization mother liquor according to the present invention may be filtrate obtained after removing psicose crystals in the crystallization process, and in addition, may further comprise washing water obtained in the crystal washing step. The psicose crystallization mother liquor may have the psicose content of 80% by weight or higher, for example, 80% by weight to 99% by weight or 85% by weight to 96% by weight, based on 100% by weight of the total solid content, and the solid content may be less than 70 Brix, for example, 60 Brix or higher to lower than 70 Brix.

(5) Recycling Process of Psicose Crystallization Mother Liquor

The psicose crystallization mother liquor obtained in the crystallization step may be utilized by being put into the separation process of psicose conversion product. Specifically, the psicose crystallization mother liquor may be recycled for preparation of psicose by being put into one or more separation processes selected from the group consisting of activated carbon treatment, ion purification and simulated moving bed (SMB) chromatography separation processes. Specifically, an example of the separation process, may perform the primary ion purification process and SMb chromatography separation process to psicose conversion product, or perform activated carbon treatment, ion purification and simulated moving bed (SMB) chromatography separation process to psicose conversion product, and before performing the SMB chromatography separation process in the separation process, selectively, may further perform a concentration process. The separation process is same as described in (2) separation process of psicose conversion reactant item.

In one embodiment, when the psicose crystallization mother liquor is put into the primary ion purification process and ion purification process is performed with psicose conversion product, it may be treated with ion purification and SMB chromatography separation processes, or treated with activated carbon treatment process, ion purification and SMB chromatography separation process in order. In addition, selectively, a concentration process may be further performed before the SMB chromatography separation process.

When the psicose crystallization mother liquor is put into the primary ion purification process or activated carbon treatment process, the psicose crystallization mother liquor mixed with psicose conversion product or products at which the activated carbon treatment process is performed may be put into the psicose separation process so that the psicose content is 15% by weight to 50% by weight, preferably 20 to 45% by weight based on 100% by weight of the total solid content of input solution before treatment of corresponding separation process.

It is preferable to perform the purification process selectively for recycling the psicose crystallization mother liquor for the psicose preparation process, but it may be put into the psicose preparation process without a separate purification process, since the mother liquor itself comprise high purity of psicose and therefore the content may be reduced due to the purification process. Thus, in order to ensure the process stability, since the psicose conversion product have relatively low content of psicose, it is preferable to perform the purification process by mixing them with the psicose crystallization mother liquor. Therefore, it is preferable to put the psicose crystallization mother liquor before the primary ion purification process treatment.

Effect of the Invention

The method for preparing psicose by recycling the psicose crystallization mother liquor obtained in the separation process of psicose preparation into the psicose separation process and the apparatus used for the same according to the present invention is a method for enhancing the purity and yield of psicose and increasing the availability of raw material, since psicose is comprised at a high concentration in the psicose crystallization mother liquor obtained in the psicose crystallization process.

BRIEF DESCRIPTION OF DRAWINGS

FIG. 1 is a diagram showing one example of general SMB process.

DETAILED DESCRIPTION OF THE EMBODIMENTS

Hereinafter, the present invention will be described in more detail with the following examples. However, these examples are only for illustrative purpose, and the scope of the present invention is not limited by these examples.

Preparative Example 1. Preparation of Psicose Syrup

A psicose syrup was prepared from a fructose substrate by the biological method substantially same with the preparation method disclosed in the Korean laid-open patent publication No. 2014-0054997.

Specifically, the encoding gene of psicose epimerase derived from *Clostridiuim scindens* (*Clostridiuim scindens* ATCC 35704) (DPE gene; Gene bank: EDS06411.1) was introduced into a recombinant vector (pCES_sodCDPE), and *Corynebacterium glutaricum* was transformed by using the prepared recombinant vector (pCES_sodCDPE) plasmid with electroporation. A bead including the transformed *Corynebacterium glutaricum* cell was prepared and packed into an immobilization reaction column, and a psicose syrup was prepared from 40 bix of 88% by weight of fructose or 95% by weight of fructose. That is, the psicose syrup of 21-23 (w/w) % of which solid mixture weight ratio of glucose:fructose:psicose:oligosaccharide is 41:39:15:5 from 88% by weight of fructose-containing substrate (psicose syrup A), and the psicose syrup of 24-26 (w/w) % of which glucose:fructose:psicose:oligosaccharide=6:67:25:2 from the raw material comprising 95% by weight of fructose content (psicose syrup B).

Preparative Example 2: Preparation of Psicose Crystallization Mother Liquor

In order to remove impurities such as colored and ion components, etc in two kinds of psicose syrups obtained in Preparative Example 1, after desalting by passing solution at the rate of twice (1-2 times) volumes of ion exchange resin per hour into the column at room temperature packed with cation exchange resin, anion exchange resin and resin in which cation exchange resin and anion exchange resin are mixed, the high purity of psicose solution was separated and collected by using a chromatography packed with calcium ($Ca^{2+}$) type of ion exchange resin. The psicose fraction comprised the psicose content of 95 to 98% by weight and the fructose raffinate comprised the fructose 85 to 95% by weight, glucose 1 to 10% by weight and reducing sugar 1 to 5% by weight, which were collected from the psicose syrup obtained from the raw material of fructose content of 88% by weight (psicose syrup A). The psicose fraction comprised the psicose content of 95 to 98% by weight and the fructose raffinate comprised the fructose 88 to 97% by weight, glucose 1 to 8% by weight and reducing sugar 1 to 4% by weight, which were collected from the psicose syrup obtained from the raw material of fructose content of 95% by weight (psicose syrup B).

The psicose fraction was concentrated at the concentration of 82Bx (%, w/w) (80-83Bx), and cooled slowly from the temperature of 35° C. (35-40° C.) at which it became supersaturated up to the temperature of 10° C. (10-15° C.), thereby generating crystals. Then the psicose seed crystals were not added, and the psicose crystals collected in the crystallization step were centrifugally dehydrated, thereby obtaining the psicose crystallization mother liquor and crystals. After the psicose crystals were washed with cooling water, they were dried and collected. The psicose crystallization mother liquor comprised the psicose content of 88 to 92% by weight. The average particle size of obtained psicose crystal powder was 237 μm, and its particle diameter range was distributed in 74-428 μm, and it had a long rectangular shape of crystal structure rhombic system.

Example 1: Production of Psicose Using Recycling of Psicose Crystallization Mother Liquor To produce 10 tons of solids of 95% by weight of psicose content by using the fructose-containing raw material solution of 88% by weight of fructose content obtained in Preparative Example 1, the psicose conversion process and separation process were carried out at flow rate 3.8 m³/hr. The psicose content of reactants collected through the psicose conversion process was 20 to 24% by weight, and they passed through the separation process at a concentration of 45 to 50% by weight after ion purification. The psicose content of psicose fraction obtained by separating it using Ca+ type separation resin was 95 to 98% by weight, and the total solids were 5 to 9% by weight. The psicose fraction was used for the crystallization process through ion purification and concentration. The psicose solution put into the crystallization process had the psicose content of 80 to 82% by weight, and it was crystallized through cooling crystallization generally used for the crystallization process. After the crystallization reaction, crystals and mother liquor which was not crystallized were separated by a dehydrator. Then the yield of crystallization was 45 to 60%. The psicose conversion reaction and crystallization method were carried out by the substantially same method with Preparative Examples 1 and 2.

The generated psicose crystallization mother liquor was recovered all and mixed with the psicose conversion reactant syrup of psicose content 20 to 24% by weight which passed the psicose conversion process, thereby maintaining the psicose content of mixture to 30% by weight. The psicose mixture with the psicose content of 30% by weight was passed through SMB chromatography separation process via ion purification. The mixture and the composition of saccharides of fructose raffinate by each process we analyzed and shown in the following Table 1.

The yield shown in the following Table 1 represented the solid content comprised in result obtained after treating the corresponding process as % by weight based on 100% by weight of solid content of input provided for the corresponding process. The content of raw material before treatment and result after treatment by each process of the following Table 1 represented the content of each compositional component as % by weight based on 100% by weight of the total solid content comprised in input or result of corresponding process.

TABLE 1

| Classification | Saccharides including disaccharides or higher degree of polymerization | Glucose | Fructose | Psicose | Reducing sugar | Yield |
|---|---|---|---|---|---|---|
| Fructose raw material | 1.1% | 5.0% | 88.1% | 0.0% | 5.8% | — |
| Psicose conversion reaction solution | 1.1% | 5.0% | 65.2% | 22.9% | 5.8% | — |
| Mixed solution of psicose conversion reaction and crystallization mother liquor | 0.6% | 3.5% | 61.8% | 30.2% | 3.9% | — |
| Reaction solution after purification/concentration | 0.6% | 3.5% | 61.8% | 30.2% | 3.9% | — |
| Psicose fraction after SMB high purity separation | 0.0% | 0.0% | 0.6% | 98.0% | 1.4% | 28.5% |
| Fructose raffinate after SMB high purity separation | 1.2% | 6.3% | 86.9% | 1.3% | 4.3% | 81.5% |
| Purification/concentration of psicose fraction | 0.0% | 0.0% | 0.6% | 98.0% | 1.4% | — |
| Psicose crystal | 0.0% | 0.0% | 0.1% | 99.9% | 0.0% | 55.2% |
| Cyrstallization motherliquor | 0.0% | 0.0% | 5.5% | 91.2% | 3.3% | 44.8% |

As shown in the Table 1, when the psicose preparation process was operated by using 88 wt % of fructose content of fructose raw material by weight based on 100% by weight of total content of solids, the psicose conversion rate represented about 23%. When the process was operated by mixing the crystallization mother liquor and setting the psicose 30% by weight, the psicose fraction obtained after conducting SMB high-purity separation had the psicose content of 95% by weight or higher. It was demonstrated that the production of high purity psicose was increased by increasing the separation yield according to raising the psicose content of raw material before treatment which was put into the SMB high purity process by recycling the psicose crystallization mother liquor.

Example 2: Production of Psicose Using Recycling of Psicose Crystallization Mother Liquor To produce 10 tons of solids of 95% by weight of psicose content by using the fructose-containing raw material solution of 88% by weight of fructose content obtained in Preparative Example 1, the psicose conversion process and separation process were carried out at flow rate 3.8 m³/hr. The psicose content of reactants collected through the psicose conversion process was 20 to 24% by weight, and they passed through the separation process at a concentration of 45 to 50% by weight after ion purification. The psicose content of psicose fraction obtained by separating it using Ca²⁺ type separation resin was 95 to 98% by weight, and the total solids were 5 to 9% by weight. The psicose fraction was used for the crystallization process through ion purification and concentration. The psicose solution put into the crystallization process had the psicose content of 80 to 82% by weight, and it was crystallized through cooling crystallization generally used for the crystallization process. After the crystallization reaction, crystals and mother liquor which was not crystallized were separated by a dehydrator. Then the yield of crystallization was 45 to 60%. The psicose conversion reaction and crystallization method were carried out by the substantially same method with Preparative Examples 1 and 2.

The produced psicose crystallization mother liquor was recovered as a whole and mixed with the psicose conversion product syrup of psicose content 20 to 24% by weight which passed the psicose conversion process, thereby maintaining the psicose content of mixture to 40% by weight. The psicose mixture with the psicose content of 40% by weight was passed through SMB chromatography separation process after ion purification. The saccharides composition of the mixture and fructose raffinate obtained by each process were analyzed and shown in the following Table 2. The yield and content indication criteria in the following Table 2 were the same those defined in the Table 1.

TABLE 2

| Classification | Saccharides including disaccharides or higher degree of polymerization | Glucose | Fructose | Psicose | Reducing sugar | Yield |
|---|---|---|---|---|---|---|
| Fructose raw material | 1.1% | 5.0% | 88.1% | 0.0% | 5.8% | — |
| Psicose conversion reaction solution | 1.1% | 5.0% | 65.2% | 22.9% | 5.8% | — |
| Mixed solution of psicose conversion reaction and | 0.3% | 2.3% | 54.7% | 40.6% | 2.1% | — |

TABLE 2-continued

| Classification | Saccharides including disaccharides or higher degree of polymerization | Glucose | Fructose | Psicose | Reducing sugar | Yield |
|---|---|---|---|---|---|---|
| crystallization mother liquor | | | | | | |
| Reaction solution after purification/concentration | 0.3% | 2.3% | 54.7% | 40.6% | 2.1% | — |
| Psicose fraction after SMB high purity separation | 0.0% | 0.0% | 0.1% | 97.6% | 2.3% | 38.4% |
| Fructose raffinate after SMB high purity separation | 1.2% | 8.6% | 84.4% | 2.2% | 3.6% | 61.6% |
| Purification/concentration of psicose fraction | 0.0% | 0.0% | 0.1% | 97.6% | 2.3% | — |
| Psicose crystal | 0.0% | 0.0% | 0.1% | 99.9% | 0.0% | 56.6% |
| Cyrstallization motherliquor | 0.0% | 0.0% | 6.8% | 90.3% | 2.9% | 43.4% |

As shown in the Table 2, when the psicose preparation process was operated by using 88 wt % of fructose content of fructose raw material by weight based on 100% by weight of total content of solids, the psicose conversion rate represented about 23%, and the psicose fraction obtained after conducting SMB high purity separation by mixing the crystallization mother liquor and setting the psicose 40% by weight had the psicose content of 95% by weight or higher. It was demonstrated that the production of high purity psicose was increased by increasing the separation yield according to raising the psicose content of raw material before treatment which was put into the SMB high purity process by recycling the psicose crystallization mother liquor.

Example 3: Production of Psicose Using Recycling of Psicose Crystallization Mother Liquor To produce 10 tons of solids of 95% by weight of psicose content by using the fructose-containing raw material solution of 95% by weight of fructose content obtained in Preparative Example 1, the psicose conversion process and separation process were carried out at flow rate 3.8 m³/hr. The psicose content of reactants collected through the psicose conversion process was 24 to 27% by weight, and they passed through the separation process at a concentration of 45 to 50% by weight after ion purification. The psicose content of psicose fraction obtained by separating it using Ca+ type separation resin was 95 to 98% by weight, and the total solids were 5 to 9% by weight. The psicose fraction was used for the crystallization process through ion purification and concentration. The psicose solution put into the crystallization process had the psicose content of 80 to 82% by weight, and it was crystallized through cooling crystallization generally used for the crystallization process. After the crystallization reaction, crystals and mother liquor which was not crystallized were separated by a dehydrator. Then the yield of crystallization was 45 to 60%. The psicose conversion reaction and crystallization method were carried out by the substantially same method with Preparative Examples 1 and 2.

The generated psicose crystallization mother liquor was recovered all and mixed with the psicose conversion reactant syrup of psicose content 24 to 27% by weight which passed the psicose conversion process, thereby maintaining the psicose content of mixture to 30% by weight. The psicose mixture with the psicose content of 30% by weight was passed through SMB chromatography separation process via ion purification. The saccharides composition of the mixture and fructose raffinate obtained by each process were analyzed and shown in the following Table 3. The yield and content indication criteria in the following Table 3 were the same those defined in the Table 1.

TABLE 3

| Classification | Saccharides including disaccharides or higher degree of polymerization | Glucose | Fructose | Psicose | Reducing sugar | Yield |
|---|---|---|---|---|---|---|
| Fructose raw material | 0.6% | 2.6% | 95.2% | 0.0% | 1.6% | — |
| Psicose conversion reaction solution | 0.6% | 2.5% | 67.4% | 26.4% | 2.5% | — |
| Mixed solution of psicose conversion reaction and crystallization mother liquor | 0.5% | 2.2% | 67.4% | 30.2% | 2.2% | — |
| Reaction solution after purification/concentration | 0.5% | 2.2% | 67.4% | 30.2% | 2.2% | — |

TABLE 3-continued

| Classification | Saccharides including disaccharides or higher degree of polymerization | Glucose | Fructose | Psicose | Reducing sugar | Yield |
|---|---|---|---|---|---|---|
| Psicose fraction after SMB high purity separation | 0.0% | 0.0% | 1.2% | 96.2% | 2.3% | 28.5% |
| Fructose raffinate after SMB high purity separation | 1.2% | 4.6% | 89.6% | 1.4% | 3.2% | 81.5% |
| Purification/concentration of psicose fraction | 0.0% | 0.0% | 0.6% | 98.0% | 1.4% | — |
| Psicose crystal | 0.0% | 0.0% | 0.1% | 99.9% | 0.0% | 53.5% |
| Cyrstallization motherliquor | 0.0% | 0.0% | 6.3% | 89.8% | 3.9% | 46.5% |

As shown in the Table 3, when the psicose preparation process was operated by using 95.2 wt % of fructose content of fructose raw material by weight based on 100% by weight of total content of solids, the psicose conversion rate represented about 26.4%, and the psicose fraction obtained after conducting SMB high purity separation by mixing the crystallization mother liquor and setting the psicose 30% by weight had the psicose content of 95% by weight or higher. It was demonstrated that the production of high purity psicose was increased by increasing the separation yield according to raising the psicose content of raw material before treatment which was put into the SMB high purity process by recycling the psicose crystallization mother liquor.

Example 4: Production of Psicose Using Recycling of Psicose Crystallization Mother Liquor To produce 10 tons of solids of 95% by weight of psicose content by using the fructose-containing raw material solution of 95% by weight of fructose content obtained in Preparative Example 1, the psicose conversion process and separation process were carried out at flow rate 3.8 m³/hr. The psicose content of reactants collected through the psicose conversion process was 24 to 27% by weight, and they passed through the separation process at a concentration of 45 to 50% by weight after ion purification. The psicose content of psicose fraction obtained by separating it using Ca+ type separation resin was 95 to 98% by weight, and the total solids were 5 to 9% by weight. The psicose fraction was used for the crystallization process through ion purification and concentration. The psicose solution put into the crystallization process had the psicose content of 80 to 82% by weight, and it was crystallized through cooling crystallization generally used for the crystallization process. After the crystallization reaction, crystals and mother liquor which was not crystallized were separated by a dehydrator. Then the yield of crystallization was 45 to 60%. The psicose conversion reaction and crystallization method were carried out by the substantially same method with Preparative Examples 1 and 2.

The generated psicose crystallization mother liquor was recovered all and mixed with the psicose conversion reactant syrup of psicose content 24 to 27% by weight which passed the psicose conversion process, thereby maintaining the psicose content of mixture to 40% by weight. The psicose mixture with the psicose content of 40% by weight was passed through SMB chromatography separation process via ion purification. The saccharides composition of the mixture and fructose raffinate obtained by each process were analyzed and shown in the following Table 4. The yield and content indication criteria in the following Table 4 were the same those defined in the Table 1.

TABLE 4

| Classification | Saccharides including disaccharides or higher degree of polymerization | Glucose | Fructose | Psicose | Reducing sugar | Yield |
|---|---|---|---|---|---|---|
| Fructose raw material | 0.6% | 2.6% | 95.2% | 0.0% | 1.6% | — |
| Psicose conversion reaction solution | 0.6% | 2.5% | 67.4% | 26.4% | 2.5% | — |
| Mixed solution of psicose conversion reaction and crystallization mother liquor | 0.3% | 1.6% | 56.3% | 40.1% | 1.7% | — |
| Reaction solution after purification/concentration | 0.3% | 1.6% | 56.3% | 40.1% | 1.7% | — |
| Psicose fraction after SMB high purity separation | 0.0% | 0.0% | 0.8% | 97.1% | 2.1% | 37.8% |

TABLE 4-continued

| Classification | Saccharides including disaccharides or higher degree of polymerization | Glucose | Fructose | Psicose | Reducing sugar | Yield |
|---|---|---|---|---|---|---|
| Fructose raffinate after SMB high purity separation | 1.0% | 4.1% | 88.6% | 3.6% | 2.7% | 62.2% |
| Purification/concentration of psicose fraction | 0.0% | 0.0% | 0.8% | 97.1% | 2.1% | — |
| Psicose crystal | 0.0% | 0.0% | 0.1% | 99.9% | 0.0% | 53.2% |
| Cyrstallization motherliquor | 0.0% | 0.0% | 6.9% | 88.6% | 4.5% | 46.8% |

As shown in the Table 4, when the psicose preparation process was operated by using 95.2 wt % of fructose content of fructose raw material by weight based on 100% by weight of total content of solids, the psicose conversion rate represented about 26.4%, and the psicose fraction obtained after conducting SMB high purity separation by mixing the crystallization mother liquor and setting 40% by weight of psicose had 95% by weight or higher of the psicose content. It was demonstrated that the production of high purity psicose was increased by increasing the separation yield according to raising the psicose content of raw material before treatment which was put into the SMB high purity process by recycling the psicose crystallization mother liquor.

The invention claimed is:

1. A method of preparation for psicose, comprising providing a psicose crystallization mother liquor into a psicose separation process to obtain psicose,
   wherein the psicose separation process comprises one or more steps selected from the group consisting of activated carbon treatment, ion purification and simulated moving bed (SMB) chromatography separation, and
   wherein the psicose crystallization mother liquor is provided into the psicose separation process and mixed with a solution in the psicose separation process to produce a mixed solution such that the content of psicose in the mixed solution before being treated by the psicose separation process is 15% by weight to 50% by weight based on 100% by weight of the total solid content.

2. The method of preparation of claim 1, wherein the psicose crystallization mother liquor is obtained by performing SMB chromatography separation of psicose conversion product to produce a psicose fraction, ion purification and concentration of the psicose fraction to produce psicose concentrates, and crystallization of the concentrates to prepare a psicose crystal.

3. The method of preparation of claim 1, wherein the psicose crystallization mother liquor is treated by being putting into the psicose separation process.

4. The method of preparation of claim 1, wherein the psicose crystallization mother liquor is treated by the ion purification and SMB chromatography separation process in order, with being put into the ion purification step.

5. The method of preparation of claim 4, wherein the activated carbon treatment step is performed, before the ion purification step.

6. The method of preparation of claim 1, wherein the psicose crystallization mother liquor is treated by the activated carbon treatment, ion purification and simulated moving bed (SMB) chromatography separation process in order, with being put into the activated carbon treatment step.

7. The method of preparation of claim 1, wherein the psicose crystallization mother liquor comprises 80% by weight or higher of psicose content based on 100% by weight of the total solid content.

8. The method of preparation of claim 1, wherein the SMB chromatography process is carried out with a column chromatograph packed with cation exchange resin having calcium active group.

9. The method of preparation of claim 1, wherein the psicose content in the psicose fraction is 85% by weight or higher based on 100% by weight of the total solid content.

10. The method of preparation of claim 1, wherein the psicose crystallization mother liquor is obtained by converting a fructose-containing raw material into psicose to produce psicose conversion product,
   treating the psicose conversion product with ion purification and the simulated moving bed (SMB) chromatography process to produce psicose fraction,
performing ion purification and concentration of the psicose fraction to produce psicose concentrate, and
   preparing psicose crystals from the concentrate.

11. The method of preparation of claim 10, wherein the psicose crystallization mother liquor is obtained by
   converting a fructose-containing raw material into psicose with using biological catalyst, to produce psicose conversion product,
   treating the psicose conversion product with activated carbon treatment, ion purification and the simulated moving bed (SMB) chromatography process to produce psicose fraction,
   performing ion purification and concentration of the psicose fraction to produce psicose concentrate, and
   preparing psicose crystals from the concentrate.

12. The method of preparation of claim 10, wherein the fructose content in fructose-containing raw material is 85% by weight or higher based on 100% by weight of the total solid content.

13. The method of preparation of claim 9, wherein the psicose conversion reaction is performed with a biological catalyst having 15% to 70% of the psicose conversion rate.

14. The method of preparation of claim 9, further comprising a step of treating fructose raffinate obtained in the SMB chromatography separation process with one or more steps selected from the group consisting of cooling, pH adjustment, ion purification and concentration processes, and recycling as a raw material of psicose conversion reaction.

* * * * *